(12) United States Patent
Berberich

(10) Patent No.: US 11,191,535 B2
(45) Date of Patent: Dec. 7, 2021

(54) SUTURING DEVICE, IN PARTICULAR FOR SUTURING LACERATIONS OF THE MENISCUS

(71) Applicant: MEDACTA INTERNATIONAL S.A., Castel San Pietro (CH)

(72) Inventor: Sascha Berberich, Tuttlingen (DE)

(73) Assignee: MEDACTA INTERNATIONAL S.A., Castel San Pietro (CH)

( * ) Notice: Subject to any disclaimer, the term of this patent is extended or adjusted under 35 U.S.C. 154(b) by 377 days.

(21) Appl. No.: 15/777,485

(22) PCT Filed: Nov. 16, 2016

(86) PCT No.: PCT/IB2016/056886
§ 371 (c)(1),
(2) Date: May 18, 2018

(87) PCT Pub. No.: WO2017/085629
PCT Pub. Date: May 26, 2017

(65) Prior Publication Data
US 2018/0368835 A1    Dec. 27, 2018

(30) Foreign Application Priority Data

Nov. 19, 2015    (IT) .................. 102015000074239

(51) Int. Cl.
*A61B 17/04*   (2006.01)
*A61B 17/06*   (2006.01)
*A61B 17/062*  (2006.01)

(52) U.S. Cl.
CPC ........ *A61B 17/0401* (2013.01); *A61B 17/062* (2013.01); *A61B 17/06166* (2013.01);
(Continued)

(58) Field of Classification Search
CPC ............ A61B 17/0401; A61B 17/0466; A61B 17/0469; A61B 2017/06052;
(Continued)

(56) References Cited

U.S. PATENT DOCUMENTS 5,810,848 A  * 9/1998  Hayhurst ............... A61B 17/04
                                                     606/139
6,818,010 B2   11/2004  Eichhorn et al.
(Continued)

FOREIGN PATENT DOCUMENTS

AU    2011201013 A1    3/2011
AU    2015202757 A1    6/2015
(Continued)

OTHER PUBLICATIONS

Australian Office Action for Application No. 2016357624. dated Jun. 21, 2018, 5 pages.
(Continued)

*Primary Examiner* — Sarah W Aleman
(74) *Attorney, Agent, or Firm* — Meunier Carlin & Curfman LLC

(57) ABSTRACT

A suturing device, in particular for suturing lacerations of the meniscus, comprising: a needle provided with a longitudinal cavity extending along a main direction; at least a first and a second member slidably inserted in the cavity and arranged in succession along the main direction; a surgical thread slidably inserted in the cavity and connected to the first and second member, wherein the first and second member each comprise at least one pair of bodies connected together by means of a junction. Other aspects may be disclosed and claimed.

10 Claims, 5 Drawing Sheets

(52) U.S. Cl.
CPC ............... *A61B 2017/0409* (2013.01); *A61B 2017/0417* (2013.01); *A61B 2017/0438* (2013.01); *A61B 2017/06052* (2013.01)

(58) Field of Classification Search
CPC ...... A61B 2017/0488; A61B 17/06166; A61B 2017/0404; A61B 2017/0406; A61B 2017/0408; A61B 2017/0409; A61B 2017/0414
See application file for complete search history.

(56) References Cited

U.S. PATENT DOCUMENTS

| | | | |
|---|---|---|---|
| 7,390,332 B2* | 6/2008 | Selvitelli | A61B 17/0401 606/144 |
| 7,651,509 B2* | 1/2010 | Bojarski | A61F 2/0805 606/139 |
| 7,658,750 B2* | 2/2010 | Li | A61B 17/0401 606/232 |
| 2004/0122456 A1 | 6/2004 | Saadat et al. | |
| 2005/0251209 A1* | 11/2005 | Saadat | A61B 17/08 606/232 |
| 2012/0101526 A1 | 4/2012 | Bennett | |
| 2013/0268001 A1 | 10/2013 | Catanese, III et al. | |
| 2015/0088198 A1* | 3/2015 | Spenciner | A61B 17/06166 606/232 |
| 2015/0351815 A1 | 12/2015 | Wales et al. | |

FOREIGN PATENT DOCUMENTS

| | | |
|---|---|---|
| EP | 1568326 A1 | 8/2005 |
| JP | 2007529279 A | 10/2007 |
| JP | 2008543509 A | 12/2008 |
| WO | WO1994015537 A1 | 7/1994 |
| WO | WO2005089658 A1 | 9/2005 |

OTHER PUBLICATIONS

Japanese Office Action for Application No. 2018-525720, dated Sep. 17, 2019, 10 pages.
International Search Report for PCT/IB2016/056886, dated Feb. 21, 2017, 2 pages.
EP Search Report issued in EP 19182145.3, dated Sep. 11, 2019.
Communication pursuant to Article 94(3) EPC issued in EP 19182145.3, dated Jun. 25, 2020.
Australian Examination Report issued in AU 2019204195, dated Mar. 12, 2020.

* cited by examiner

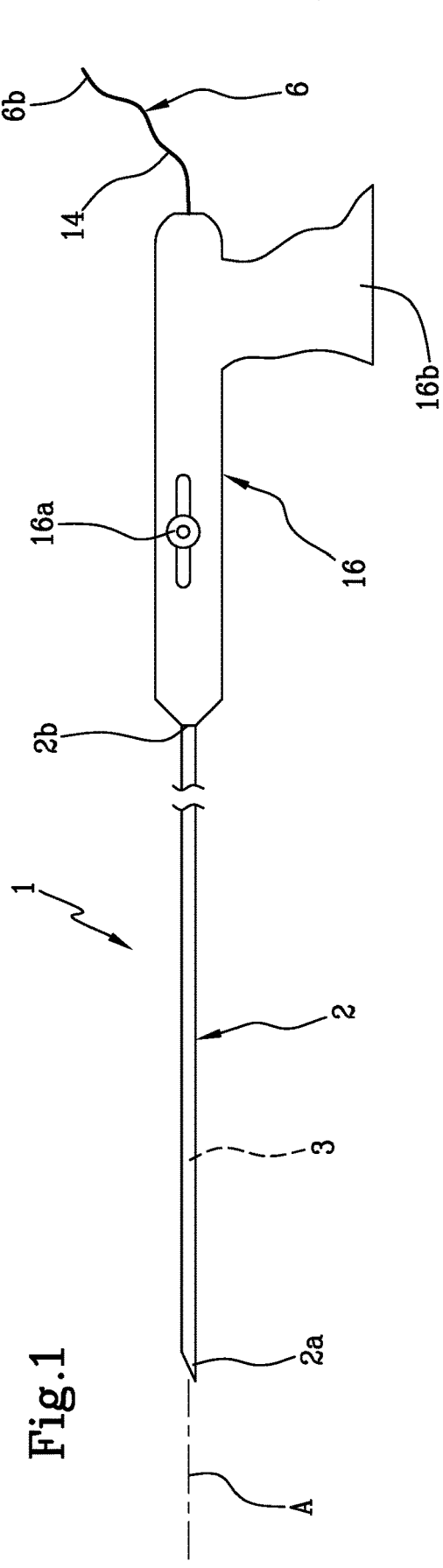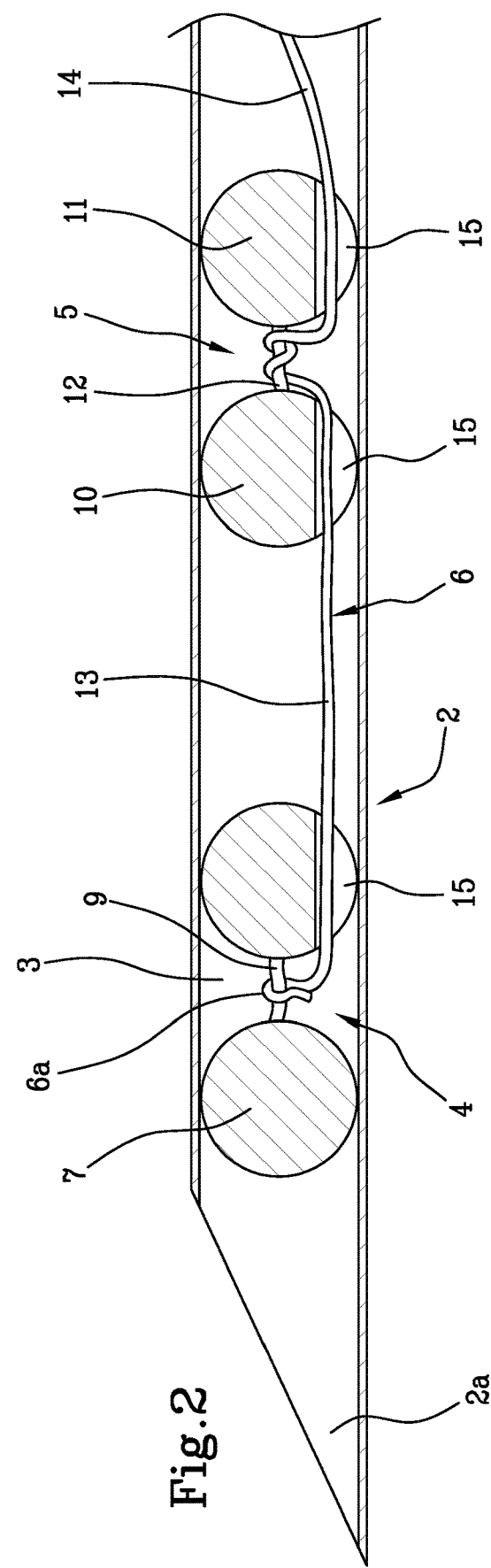

Fig.4
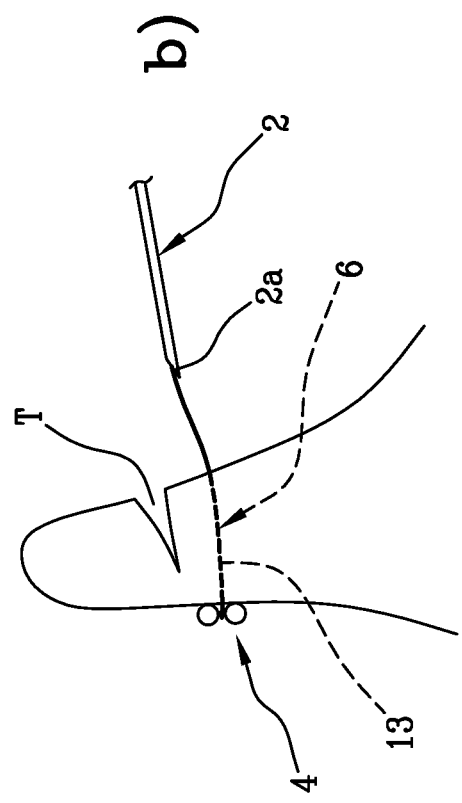
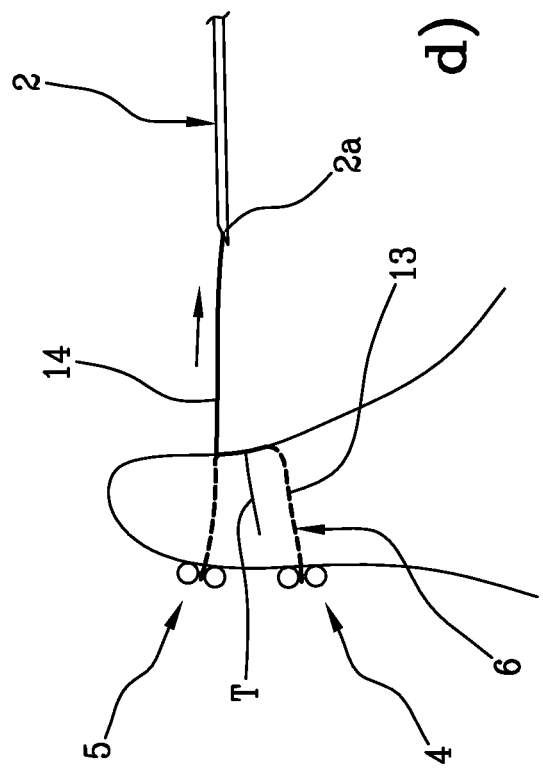
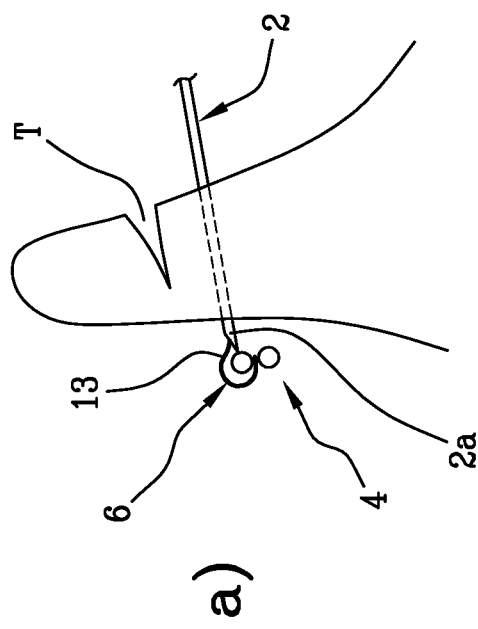
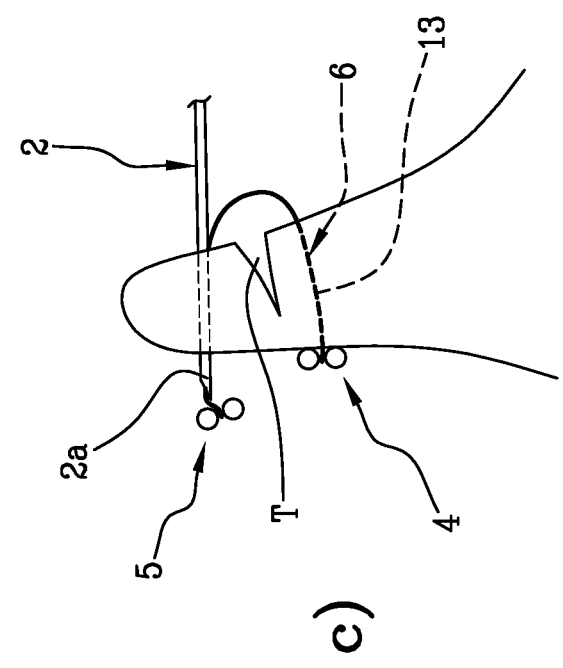

SUTURING DEVICE, IN PARTICULAR FOR SUTURING LACERATIONS OF THE MENISCUS

The present application is a National Phase Entry of PCT International Application No. PCT/IB2016/056886, which was filed on Nov. 16, 2016, and which claims priority to application No. 102015000074239 filed in Italy on Nov. 19, 2015, the contents of which are hereby incorporated by reference.

The present invention relates to a suturing device, in particular for suturing lacerations of the meniscus.

Therefore, the present invention finds particular application in the medical and biomedical fields, especially in the designing and manufacturing of instruments for arthroscopic surgery.

In fact, one of the most common operations at the orthopaedic level is repairing lacerations of the meniscus, in particular lacerations occurring on the sides of the meniscus and that need to be sutured in due time in order to prevent them from deepening and thus portions of the meniscus from detaching.

In prior art instruments for repairing the lacerations of the meniscus by using arthroscopy are known, some of which allow to suture such lacerations in a short time and with extreme precision.

One of the best-known systems to perform these operations is marketed by Smith & Nephew® and involves the use of a grooved needle slidably inserted into a cannula and to which a surgical thread and two members or retainer bodies are associated.

In particular, the first and the second members are defined by the respective metal plates arranged in succession along the needle and slidably connected to it; both these plates are associated to the surgical thread.

Operationally, the surgeon inserts the cannula into the patient's knee with a predetermined angle and, by means of suitable manoeuvring means, moves the needle in order to pierce the meniscus in two places situated on two opposite points of the laceration (transversally or longitudinally).

Following each perforation, one of the above members is released (it is done always by using manoeuvring means) on the outside of the meniscus so that it defines an abutment that allows to tension the surgical thread along the laceration, thus suturing it.

For this reason, the surgical thread comprises at least a looped and knotted portion with a kind of slip knot between the two members, so that after placing both members on the external side of the meniscus, the pull of the free end of the thread creates a "pulley" effect on said ring-shaped portion thus allowing to occlude the laceration by pulling together its flaps.

Note that the plates have a substantially rectangular shape and are edgewise housed in the needle (and in the cannula), so that their lying plane is parallel to the development direction of the cannula.

Therefore, the "short" side of each plate has a suitable size to be housed inside the sheath and the "long" side is long enough to distribute the effort on the meniscus without applying overpressure points close to the laceration.

Therefore, following the release, such plates tend to rotate on the surface so that their flat surface abuts on the meniscus.

Disadvantageously, this solution has some drawbacks, related to both the plates structure and the arrangement of the thread.

First, the planar shape of the plates results in the occurrence of high stress along their perimeter, and thus additional lacerations of the meniscus may occur.

Furthermore, the possibility that the plate can be abutted on the meniscus in a non perfectly planar configuration, although unlikely, makes it delicate to assemble the device.

Moreover, the need to linearly move the plates substantially obliges the manufacturer to use a grooved needle that acts as a guide/rail for the plate itself, and the cannula must be compulsorily inserted in order to maintain the members and the thread isolated from the external environment.

Moreover, the fact that the needle occupies most of the space within the cannula, thus making it unusable for any other purpose, greatly limits the thread diameter that can be used, which is typically no greater than 2-0 on the USP scale.

Disadvantageously, the use of such a thin surgical thread increases the concentration of efforts and as a result it is likely to cause a cutting effect when pulling.

This is especially true if the "pulley effect" is taken into consideration, which occurs after the thread is pulled because of the presence of the loop and the "slip" knot, where many portions of the length of the thread run along the tissues and might damage them.

A further device for suturing of lacerations of the meniscus is known from the publication AU2015202757, in which the members are defined by the surgical thread, in particular by stretches of the thread that have been knotted so that, as a result of pulling, a ball of thread is created and is able to define an abutment.

This solution, although theoretically interesting, has the disadvantage of complicating the realization of the device and making it difficult to manoeuvre it, since pulling or pushing movements at imprecise moments might lead to the compaction or the wrong knotting of the thread.

The object of the present invention is therefore to provide a suturing device, in particular for suturing lacerations of the meniscus, that is able to overcome the above mentioned drawbacks of the prior art.

In particular, the object of the present invention is to provide a high performing and easy to realise suturing device.

Moreover, the further object of the present invention is to provide a reliable and safe suturing device.

Said objects are reached by a suturing device, in particular for suturing lacerations of the meniscus, having the characteristics of one or more of the subsequent claims, in particular comprising a needle provided with a longitudinal cavity, at least a first and a second member slidably inserted in said cavity and arranged in succession and a surgical thread slidably inserted in said cavity and connected to said first and second member.

According to a first aspect of the present invention, the first and the second members each comprise at least a pair of bodies connected together by means of a junction element.

Preferably, these bodies are substantially spheres or substantially spherical bodies.

Therefore, each member includes a pair of spheres connected one to the other by means of a junction element.

Advantageously, in this way each pair of spheres, upon releasing, abuts on the external side of the meniscus, it defines an abutment but limits the maximum efforts.

Moreover, preferably, each sphere has a diameter that substantially corresponds to an inner diameter of the cavity.

Therefore, advantageously, the use of the spheres allows to minimize the needle size and maximize the size of the members.

In this respect, it should be noted in fact that the first and the second members (i.e. all spheres) are entirely contained in the needle cavity; in particular, each pair of spheres comprises a first and a second sphere arranged one next to the other along said cavity.

Furthermore, the thread too is positioned in the needle, at least in the portion associated to the members, thus making the presence of the containment cannula superfluous and allowing the realization of a more essential device with minimization of its size.

Preferably, to allow a better grip, the junction element between the bodies (i.e. the spheres) of each member is flexible.

A further aspect of the present invention resides in the connection between the surgical thread and the members that, as described above, was often a delicate aspect in the prior art upon pulling/suturing.

According to this (optional and stand-alone) aspect of the invention, in fact the surgical thread is slidably associated to said second member so that, following the pulling by the surgeon, the thread portion interposed between the two members shortens, thus suturing the laceration.

Preferably, the surgical thread is constrained to the member in correspondence to the respective junction element by means of a knot or wrapping in which the thread is maintained sliding.

Therefore, the knot or wrapping stays in correspondence to the second member and it remains there even after the pulling, whereas the surgical thread linearly develops between the two members without further knotted portions.

Advantageously, the knot or wrapping remains so positioned on the second member also as a result of pulling on the part of the surgeon, thus eliminating the risk of damage to the tissues that occur in the prior art and are due to the movement or sliding of the knot.

Note that, in an alternative application, a device according to the present invention may find application using the members as bone anchors.

Advantageously, in fact, by depositing the two bodies in succession inside the bone cavity (realized by means of a suitable tool/milling cutter) and then by pulling, the overall size of the two bodies (i.e. the two spheres) prevents them from sliding out of the cavity and guarantees the endurance of the suture.

These characteristics and the corresponding technical advantages will become more apparent from the following exemplary, and therefore non-limiting description of a preferred, and therefore not exclusive, embodiment of a suturing device, in particular for the suturing of lacerations of the meniscus, as described in the attached drawings, where:

FIG. 1 shows a schematic view of a suturing device, in particular for the suturing of lacerations of the meniscus according to the present invention;

FIG. 2 shows a schematic cross-sectional view of part of the device of FIG. 1;

FIGS. 4a-4d show a schematic sequence of surgical steps performed by using the suturing device of FIG. 3;

Figure 3:
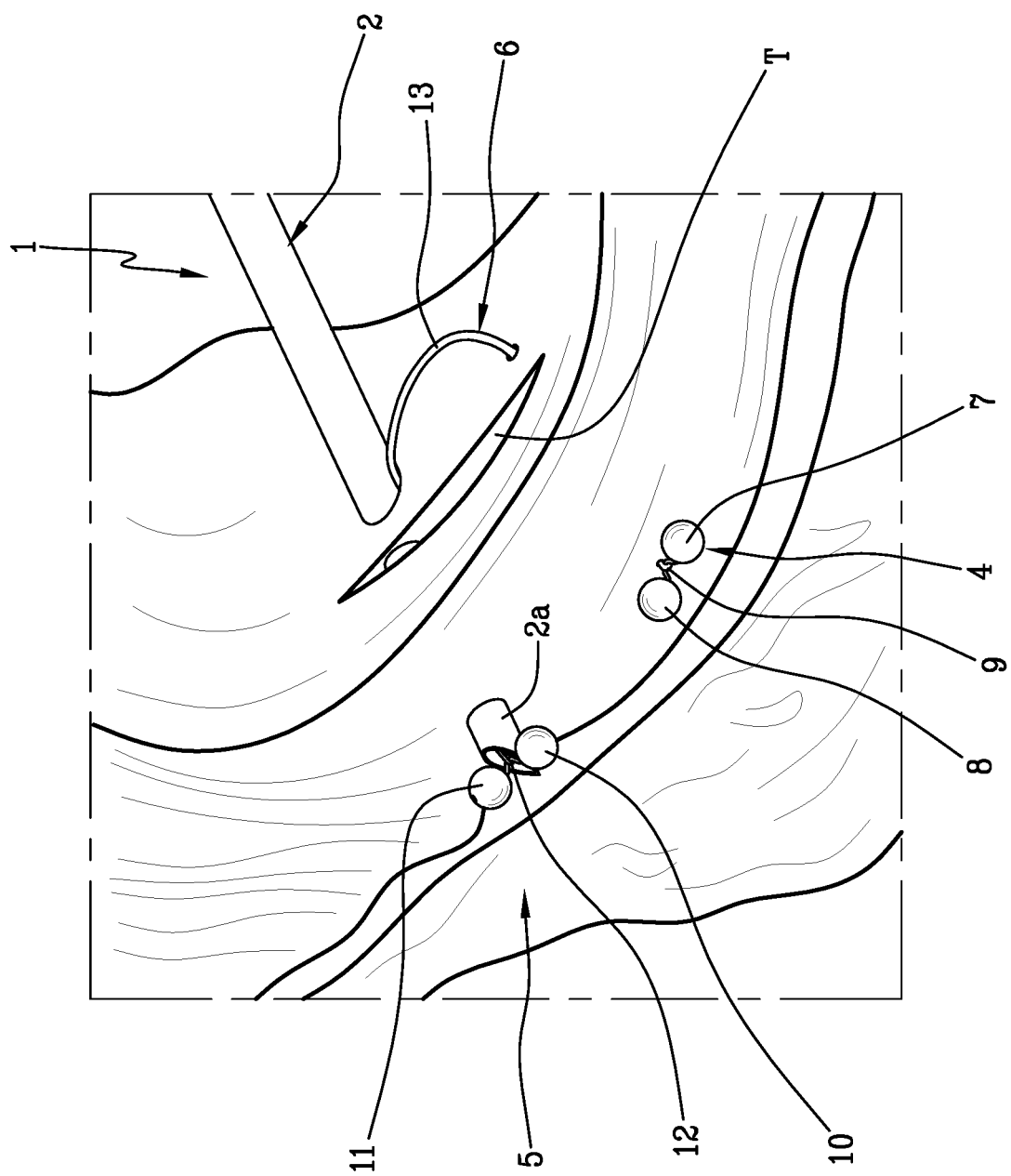
FIG. 3 shows a perspective view of a suturing device, in particular for the suturing of lacerations of the meniscus that is being used.
Figure 5:
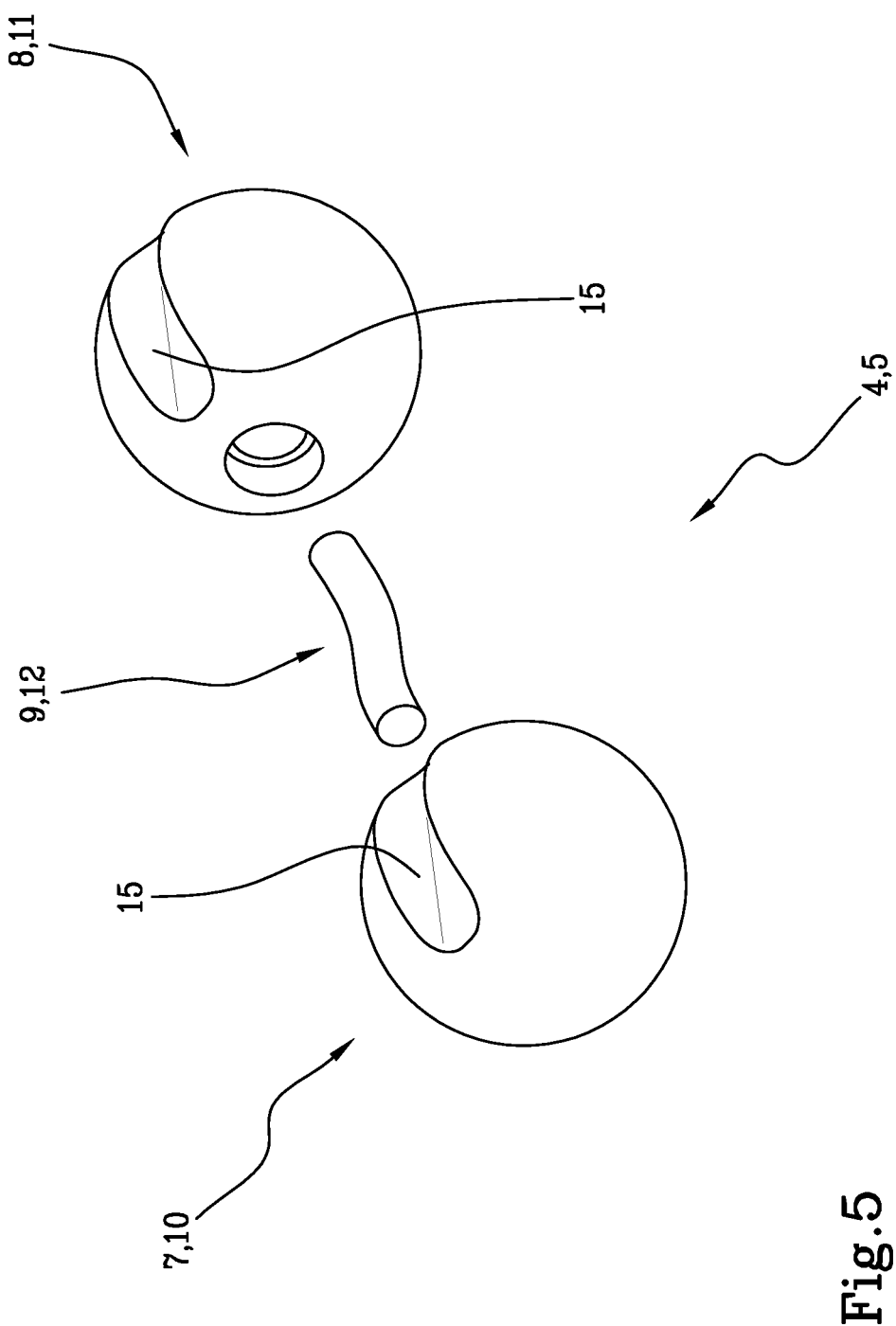
FIG. 5 shows a special suturing device, in particular for the suturing of lacerations of the meniscus according to the present invention.
Figure 6:
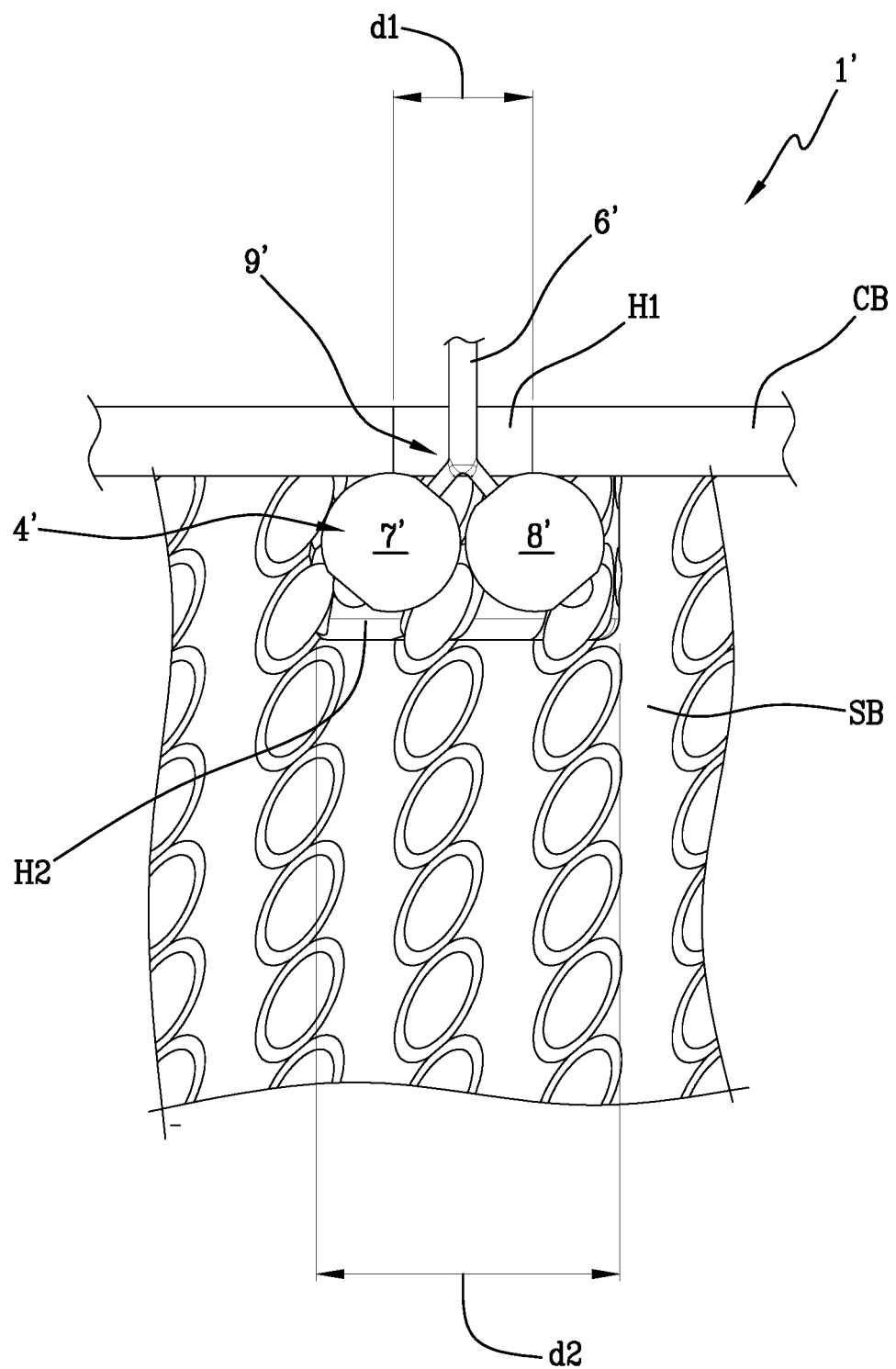

FIG. 6 schematically shows a suturing device according to the present invention in an alternative application.

With reference to the appended figures, number 1 indicates a suturing device, in particular for suturing lacerations of the meniscus, according to the present invention.

Device 1 is therefore mainly used in the orthopaedic sector, preferably when arthroscopic surgery or semi-open technique are used for repairing the meniscus.

Such a device therefore comprises at least one needle 2 extending along its own main direction "A" and provided with a longitudinal cavity 3.

The needle 2 has a first operational and pointed end portion 2a, and a second end portion 2b, preferably connected to the handle of the device 1. Note that the first end portion 2a may have a rectilinear orientation, aligned with the remaining part of the needle, or a curved orientation, with a variable angle according to the needs of the surgeon and lacerated area that needs suturing.

Preferably, the needle 2 is a substantially tubular body and the longitudinal cavity 3 is of the through type, which also extends along the main direction "A" between a first opening located at the first end portion 2a and a second opening located at the second end portion 2b.

Therefore, the cavity 3 is a duct laterally occluded by the needle wall and accessible from the openings.

A first 4 and a second 5 member, as well as a surgical thread 6 are housed (or can be housed) Inside the needle 2, in particular inside the cavity.

The members 4, 5 are shaped bodies to define an abutment to abut the outer wall of the meniscus during the pulling of the thread.

Preferably, these first 4 and second 5 members are slidably inserted into the longitudinal cavity 3 of the needle 2.

More preferably, the first 4 and second 5 members are completely contained in the cavity 3 of the needle 2.

Moreover, such members 4, 5 are arranged in succession along the main direction "A".

Such members 4, 5 are also mutually connected through the surgical thread 6, which is also slidably inserted into the cavity 3 (as it will be better explained hereinafter).

According to one aspect of the present invention, the first 4 and the second 5 members each comprise at least a pair of bodies 7, 8, 10, 11 connected together by means of a junction element 9, 12.

Preferably, the bodies are each defined by a sphere 7, 8, 10, 11 or a substantially spherical body.

Note that, in the spirit of the present invention, by using the term "sphere" what is not intended is restricting the conformation of the elements constituting the members to perfectly spherical bodies, but those "substantially spherical" elements, having an oval or ovoid shape, are also encompassed, since they may as well meet the specifications of the present invention.

In other words, in its most generic sense, the term sphere is used here to simply define a "rounded, preferably spherical body".

Therefore, the first member 4 comprises a first 7 and a second 8 sphere (or first and second body) that are connected one to the other by means of a special junction element 9.

In the same way, the second member 5 comprises a first 10 and a second 11 sphere (or first and second body) that are connected one to the other by means of a special junction element 12.

Preferably, such spheres 7, 8, 10, 11 have a diameter (or more generically a transverse size) substantially corresponding to an inside diameter of the cavity 3.

In other words, the spheres 7, 8, 10, 11 are substantially shaped for the cavity 3.

Therefore, these spheres 7, 8, 10, 11 are substantially inserted to fit in the cavity 3.

In the preferred embodiment of the invention, the spheres (or bodies) 7, 8, 10, 11 are made of polymeric material, more preferably of Poly-Ether-Ether-Ketone (PEEK) or Poly-L-lactide-co-D, L-lactide (PLDLLA).

The junction element 9, 12 is a bridge that connects the two spheres 7, 8, 10, 11 (or the two bodies) of each member 4, 5.

In certain embodiments, such a junction element 9, 12 is flexible to allow a relative movement between said spheres (or bodies) 7, 8, 10, 11 of each member 4, 5.

For example, such a junction element 9, 12 can be made of a portion of surgical thread, preferably a multi-filament suturing thread.

Alternatively, in an embodiment that is not illustrated, the junction element comprises a rigid pin extending between two ends each secured to a respective sphere.

In this embodiment, the junction element acts as a spacer between the two spheres of the individual member.

Preferably, the surgical thread 6 is slidably associated to said second member 5, more preferably (but not necessarily) to the junction element 12 of the member.

In the preferred embodiment, in fact, the surgical thread 6 is associated to said second member 5 in correspondence of the respective junction element 12 by means of a knot or wrapping in which the thread 6 is maintained sliding.

Therefore, the thread 6 is slidably constrained to the junction element 12 so as to slide along the thread by varying the length of the thread portion 6a interposed between the first 4 and the second 5 member, thus allowing the laceration to be sutured.

In other words, the thread defines the knot or wrapping that remains substantially in position on the second member 5 (or on the junction element 12), but it is slidable in such a way that the thread portion 6 defining the knot or the wrapping, changes upon pulling by the surgeon.

Therefore, the knot or wrapping does not move, whereas the thread 6 that defines it, is slidable.

In the preferred embodiment, this sliding knot or wrapping is a double thread point or the likes.

Advantageously, in such a way the knot does not move along the tissues, but the thread 6 only moves linearly, which greatly reduces friction and the wear action of the thread.

Therefore, the surgical thread 6 extends between a first end portion 6a constrained to the first member 4, and a second end portion 6b, in use externally projecting to an end opposite the needle tip 2, or externally projecting to the second end portion 2b.

More in detail, the thread 6 comprises a first suturing portion 13, interposed between the first 4 and the second 5 member having a variable length, and a second pulling portion 14, which develops between the second member 5 and the second end portion 6b.

Preferably, the second end portion 6b can be held by the surgeon to pull the thread 6b, thus allowing the sliding thereof with respect to the second member 5 and reducing the length of the first portion 13 for suturing the laceration.

Note that the first portion, the junction between the two members 4, 5, has a substantially linear development, i.e. without the presence of knots or wrapping between the two members 4, 5.

In fact, the only functional knot or wrapping in the thread 6 is located at the second member 5, in particular at the junction element 12.

With the expression "functional knot or wrapping", what is meant is the knot or wrapping that is able to perform an additional function other than the function of keeping together the two elements, e.g. allowing the sliding of an element (thread 6) in relation to the other element (junction element 12).

In the illustrated embodiment, in fact, the thread also has a fixing knot at its first end portion 6a to immovably constrain the same thread 6 to the junction portion 9 of the first member 4.

Note that the at least second sphere 8 of the first member 4 and spheres 10, 11, of the second member 5 have a peripheral groove 15 for housing the surgical thread 6 so as to minimize the size of the needle 2.

In particular, the grooves 15 extend along the main direction "A" of the needle 2 and are accessible peripherally so as to house the thread 6 when the members are inside the needle 2, thus allowing its release after sliding out. Preferably, all the spheres are equipped with such a groove 15.

Advantageously, in such a way it is possible to simultaneously minimize the size of the needle 2 (or the cavity 3) and maximize the size of the surgical thread 6 (which can substantially reach the value for the sphere radius).

Preferably, in fact, the surgical thread 6 presents a gauge between 2-0 and 0 on the USP scale, or preferably equal to 0 on the USP scale (about 0.350-0.399 mm).

Associated to the second end portion 2b of the needle 2, what is envisaged are movement means 16 of the first 4 and second 5 member configured to translate each member 4, 5 from a rest position, in which it is housed inside the cavity 3 of the needle 2 to an operating position, in which it is proximal to or externally projecting from the tip of the needle 2.

Therefore, the movement means 16 comprise at least one distal actuating member 16a from the tip (or from the first end portion 2a) of said needle 2 and operable by a user.

Therefore, the movement means 16 are projecting from the second end portion 2b of the needle 2 and comprise both a handle 16b and said actuating member 16a.

Preferably, the actuating member comprises at least a pusher element (not shown) slidably inserted into the needle 2 (or in the cavity) to get hold of the members 4, 5 and drive them from the rest position to the operating position.

Moreover, such actuating member is also provided with a control portion, proximal to the handle, that can be used by a user (i.e. the surgeon) for manoeuvring the pusher element.

Note that the pusher element is movable in at least three configurations, namely a first configuration in which both members are in the rest position, a second configuration in which the first member is in the operating position and the second member is in the rest position (or in an intermediate position between the two) and a third configuration in which both members are in the operating position.

With reference to FIG. 6 an alternative application of the device 1' is shown according to the present invention.

In this application, the member 4' is used as a bone anchor, for example for attaching tissues such as tendons.

Operationally, the procedure or graft procedure is comparable to what has been described up to now, the only difference is related to the need to preliminarily drill the bone cortical tissue "CB" giving access to the organic component "SB" of the bone, i.e. the soft bone tissue.

More precisely, in this embodiment the method envisages to drill a hole in the bone by means of a tool able to realize an undercut "UC" between the cortical tissue "CB" and the bone organic component "SB".

Therefore, downstream of the drilling, the cortical tissue "CB" has a through hole "H1" of diameter d1, whereas the bone organic component "SB" has a cavity "H2" substantially concentric to the hole "H1" and having a diameter d2 greater than diameter d1.

Alternatively, a similar procedure may provide for the drilling of a through-hole in the bone such as to have just one through-hole "H1" of diameter d1; in such an alternative the member 4' is not placed inside the bone cavity, but outside it, so as to define, for example, an anchor for the new fixing of the bone in the event of fracture.

Therefore, in the present embodiment, the device is inserted in the hole "H1" so as to pass completely through the bone (anchor for the new fixing of the bone) or for access to the cavity "H2" (anchor for tissue fixation), without substantial modifications in the operating principle and in the structure of the device.

For this reason, explicit reference will be hereinafter made to just one embodiment illustrated in FIG. 6 (tissue fixation), in which after the drilling of the bone the device 1', the needle in particular, is inserted into the cavity "H2".

Note that in this application, given the absence of a direct drilling by the device 1', the needle can be equivalently replaced by a tubular (or semi-tubular) body devoid of a tapered portion, whose only purpose is allowing the sliding of members on the inside.

Structurally, moreover, this embodiment of the device 1' may comprise a single member 4' (formed by two bodies 7', 8') insertable into the cavity "H2".

Preferably, the single member 4' is formed by at least two bodies 7 and 8' connected to one another by a junction element 9'.

The suturing thread 6' is fixed to said junction element 9', preferably in a middle portion of said element.

In this manner, after inserting the two bodies 7', 8' one after the other in the cavity "H2" through the tubular body, upon pulling the suturing thread 6' toward the outside of the same cavity "H2" the corresponding rotation of the two bodies 7', 8' in the cavity "H2" occurs, so that they are placed one next to the other and they cannot pass through the hole "H1".

In this regard, in fact, the two bodies 7', 8' each have a transverse size shorter than the hole diameter "H1" so that they can enter the cavity "H2", but which, after being added to the size of the other body, is longer than the diameter of the hole "H1", so as to be able to define the fixing anchor that is used by the surgeon, for example, to connect a tendon to the bone.

Preferably, and in accordance with what has been described, the two bodies 7', 8' are spheres.

The junction element 9' is preferably a flexible/elastic body that allows a simple rotation and does not hinder insertion.

Preferably, each body 7', 8' has a through hole within which an end of the junction element 9' is inserted.

More preferably, the junction element 9' has enlarged portions at its ends, so as to interfere with the edges of the corresponding through hole, thus preventing the body 7', 8' from sliding.

In the preferred embodiment, the junction element develops substantially into the "V" shape, i.e. it has two angled portions extending between two free ends and a common vertex.

In particular, the two free "V" ends are each connected to a respective body 7', 8'.

Preferably, the vertex is connected to the suturing thread 6'.

In the preferred embodiment, the suturing thread 6' and the junction element 9' are made in one piece. This allows to guarantee the correct positioning of the thread 6' with respect to the junction element 9' and therefore to facilitate rotation inside the cavity "H2".

Alternatively, however, the thread 6' may be knotted or secured (also slidably) to the junction element 9' in some other way.

Structurally, therefore, the device 1' according to the present invention used as a bone anchor could be simplified (no needle and member reduction), without thereby deviating from what is the spirit of the present invention, of which, therefore, such application is fully part.

In this respect, therefore, everything that has been previously described in relation to the suturing device for suturing lacerations of the meniscus and compatible with the application of the herein discussed bone anchor is also applicable, both structurally and procedurally.

The invention achieves the intended objects and provides important advantages.

In fact, the use of members comprising (at least in part) pairs of spheres connected together by means of junction elements allows on the one hand to minimize the efforts on the tissues after suturing the laceration and on the other hand to minimize the size of the needle.

Moreover, by being able to fully insert both the members and the thread inside the needle (a tubular and not grooved needle) there is no need to provide the device with a containment tube, thus making it a more compact and simple device.

Furthermore, by providing the spheres with an adequate groove what is possible is increasing the size of the surgical thread up to substantially the size of the radius of each sphere, thus allowing to reach even the gauge=or the upper gauge.

Again, the absence of knots between the two members and the substantial absence of annular wrappings between the knot and the second member makes less critical and less invasive the pulling phase and suturing of the laceration, as the friction of the thread on the tissues is greatly reduced.

The invention claimed is:

1. A suturing device, in particular for suturing lacerations of the meniscus, comprising:
   a needle provided with a longitudinal cavity extending along a main direction;
   at least a first member and a second member that, in a rest position, are slidably inserted in the cavity and arranged in succession along the main direction; and
   a surgical thread slidably inserted in the cavity and connected to the first member and the second member;
   wherein the first member and the second member each comprise at least one pair of bodies, the at least one pair of bodies of the first member being connected together by a first junction element and the at least one pair of bodies of the second member being connected together by a second junction element, wherein each pair of the bodies comprise a first and a second sphere that, in the rest position, are arranged in succession along the cavity;
   wherein the surgical thread is slidably associated to the second junction element and wherein at least the second sphere of the first member and the spheres of the second member have a peripheral groove that is configured to house the surgical thread so as to minimize the size of the needle in said rest position of the first and second member and release the surgical thread after the members slide out of the needle.

2. The suturing device according to claim 1, wherein the needle is tubular and the cavity is of the through type; each of the spheres of each member has a diameter corresponding to an inner diameter of the cavity.

3. The suturing device according claim 1, wherein the first and second member are entirely contained in the cavity of the needle.

4. The suturing device according to claim 1, wherein the first and second junction elements are flexible.

5. The suturing device according to claim 1, wherein the surgical thread is constrained to the second member in correspondence of the second junction element by a knot or wrapping.

6. The suturing device according to claim 1, wherein the thread extends between a first and a second end portion and comprises:
   a first suture portion, extending from the first end portion to a position located between the first and the second member;
   and a second pulling portion, which develops between the second member and the second end portion;
   wherein both portions are of variable length according to a pulling action performed on the second end portion.

7. The suturing device according to claim 6, wherein the first portion of the thread is linear and knot-free or has a single knot for fastening on the first junction element.

8. The suturing device according to claim 1, wherein the suturing device comprises movement means for the first and second member configured to translate each member from the rest position, in which it is housed inside the cavity of the needle, to an operating position, in which it is proximal to or externally projecting from a tip of the needle.

9. The suturing device according to claim 8, wherein the movement means comprise at least one actuating member distal from a tip of the needle and operable by a user.

10. The suturing device according to claim 1, wherein the surgical thread has a gauge of 0 according to the USP scale.

* * * * *